United States Patent
Stengele et al.

(10) Patent No.: US 6,552,182 B2
(45) Date of Patent: Apr. 22, 2003

(54) METHOD FOR PHOTOLYTICALLY DEPROTECTING IMMOBILIZED NUCLEOSIDE DERIVATIVES, ESPECIALLY IN THE PRODUCTION OF DNA CHIPS

(75) Inventors: Klaus-Peter Stengele, Pleiskirchen (DE); Heinrich Giegrich, Waldkraiburg (DE)

(73) Assignee: Nigu Chemie GmbH, Waldkraiburg (DE)

( * ) Notice: Subject to any disclaimer, the term of this patent is extended or adjusted under 35 U.S.C. 154(b) by 0 days.

(21) Appl. No.: 09/948,537

(22) Filed: Sep. 10, 2001

(65) Prior Publication Data

US 2002/0053508 A1 May 9, 2002

Related U.S. Application Data

(63) Continuation of application No. PCT/EP00/02197, filed on Mar. 13, 2000.

(30) Foreign Application Priority Data

Mar. 11, 1999 (DE) .......................................... 199 10 808
Nov. 5, 1999 (DE) .......................................... 199 53 289

(51) Int. Cl.[7] ........................ C07H 21/04; C07H 21/02; C12Q 1/68; C12P 19/34; C12M 1/34
(52) U.S. Cl. ...................... 536/25.3; 536/22.1; 536/231; 536/24.3; 536/24.31; 536/24.32; 536/24.33; 435/6; 435/7.1; 435/91.1; 435/91.2; 435/287.2
(58) Field of Search .............................. 435/6, 7.1, 91.1, 435/91.2, 287.2; 536/22.1, 23.1, 24.3–24.33

(56) References Cited

U.S. PATENT DOCUMENTS 5,658,734 A    8/1997   Brock et al.

FOREIGN PATENT DOCUMENTS

WO    WO 98/39348    9/1998

OTHER PUBLICATIONS

G. H. McGall, et al.: The Efficiency of light–directed synthesis of DNA arrays on glass substrates J. Am. Chem. Soc., vol., 119, No. 22, 1997, pp. 5080–5090 XP000775689.

*Primary Examiner*—Jeffrey Siew
(74) *Attorney, Agent, or Firm*—Sughrue Mion, PLLC

(57) ABSTRACT

The invention relates to a method for the specific photolytic deprotection of nucleoside derivatives that are immobilized on a substrate, especially for use in the production of DNA chips. Said method is characterized in that a gel or viscous liquid layer is applied on the nucleoside derivatives that are immobilized on a substrate. Said gel or viscous liquid contains one or more polymer compounds and at least one representative from the group comprising water, water/$C_1$–$C_4$ alcohol mixtures and polar aprotic solvents. For initiating the deprotection, the nucleoside derivates are irradiated. This method favors a rapid, clean and complete removal of the photolabile protective groups from the nucleoside derivatives, which results in the required purity of the synthesized nucleotide or oligonucleotide sequences.

23 Claims, No Drawings

METHOD FOR PHOTOLYTICALLY DEPROTECTING IMMOBILIZED NUCLEOSIDE DERIVATIVES, ESPECIALLY IN THE PRODUCTION OF DNA CHIPS

This is a continuation application of International Application No. PCT/EP00/02197 filed Mar. 13, 2000, the disclosure of which is incorporated herein by reference.

The present invention relates to a method for the specific photolytic deprotection of nucleoside derivatives that are immobilized on a substrate, especially in the photolithographic production of DNA chips.

For reasons of parallelization and miniaturization, DNA chips for analytic and diagnostic applications in molecular biology, medicine and related fields are commonly produced by means of photolithographic techniques. In these techniques the nucleoside derivatives are immobilized with photo labile protective groups on suitable substrates. Then the deprotection is specifically carried out by photolysis. Due to the lack of post-synthetic purifying methods, the requirements made of the chemical compositions of the protective groups are very high.

In correspondence with prior art, two methods are available for carrying out the photolytic deprotection of the protective groups. In the first method, the DNA chips are exposed by means of a suitable solvent or mixture of solvents in a flow chamber (cf. G. H. McGall, A. D. Barone, M. Diggelmann, S. P. A. Fodor, E. Gentalen, N. Ngo, J. Am. Chem. Soc. 1997, 119, 5081–5090). In this method, the substrate (e.g. in the form of a glass substrate) with the immobilized nucleoside derivatives is mounted in a flow chamber. Throughout the irradiation, a suitable mixture of solvents is pumped through the flow chamber so as to wet the synthesis side of the substrate such that the immobilized growing DNA chains are quasi present in dissolved form. Hence, the participation of the solvent or the mixture of solvents during the photo controlled deprotectioning operation is ensured in any case. Owing to its structure, the chip surface is exposed from the "wrong side", i.e. from the rear side through the substrate (e.g. in the form of glass substrates).

This method entails some disadvantages. For example, the diffusion of light on the glass substrate gives rise to a bad optical resolution. Moreover, the heating of the substrate as well as an insufficient wetting of the substrate surface may result in thermal and secondary photolytic reactions. As the photo labile protective group to be separated is quasi located on the other end of the optical path, the oligo nucleotide chain ahead of it may have the function of a light filter, which involves, on the one hand, the inherent risk of secondary photolytic reactions and, on the other hand, is apt to give rise to an extension of the exposure time.

In the second known method for the photolithographic production of DNA chips, the chips are exposed from the "correct" side, i.e. from the front side, without using a solvent (cf. M. C. Pirrung, L. Fallon, G. McGall, J. Org. Chem. 1998, 63, 241–246). Experience has shown that a particular disadvantage in this method is the poor quality of the synthesized oligo nucleotides, which must be attributed to a slow and incomplete deprotection of the nucleoside derivatives as well as to secondary thermal or photolytic reactions.

The present invention was therefore based on the problem of developing a method for the specific photolytic deprotection of nucleoside derivatives immobilized on a substrate, particularly of protective groups common in the production of DNA chips, which does not present the aforementioned disadvantages of prior art but rather permits the rapid and complete deprotection.

This problem is solved in accordance with the present invention by the provision that prior to photolysis a layer of a gel or a viscous liquid of polymer compounds in water, a water/$C_1$–$C_4$ alcohol mixture and/or a polar aprotic solvent is applied onto the substrate with the nucleoside derivatives to be deprotected.

It was a surprise to find that in this manner secondary thermal and photolytic reactions are largely repressed so that the synthesized nucleoside or nucleotide sequences present the required purity.

In the context of the inventive method, the expression "specific photolytic deprotection" is to be understood to denote the specific photolytic deprotection of the protected nucleoside derivatives. Within the scope of the present invention, it is therefore possible to separate only part of the photo labile protective groups, for instance by means of masks, in addition to the complete deprotection.

In the method according to the present invention, a layer of a gel or a viscous liquid of one or more polymer compounds in water, a mixture of water/$C_1$–$C_4$ alcohol and/or a polar aprotic solvent is applied to the substrate surface, i.e. the substrate with the immobilized nucleoside derivatives consisting of nucleosides, nucleotides or oligo nucleotides before the exposure of the nucleoside derivatives commences, preferably from the front side. The thickness of the gel layer or the layer of the viscous liquid, respectively, may be varied within wide limits, but it has been found to be of advantage for an optimum optical resolution to set the thickness of the layer to a value between 0.1 $\mu$m and 5 mm, more preferably 10 $\mu$m to 5 mm.

Preferably the fraction of polymer compounds should amount to 0.1 to 40% by weight, more particularly 1 to 20% by weight, relative to the total weight of the gel or viscous liquid, respectively. In accordance with a preferred embodiment, such polymers are used for the build-up of gels presenting a sol/gel transition temperature of 15 to 90° C., particularly 30 to 50°C. The advantage of these gels resides in the fact that they are quasi solid at room temperature and can be converted into the liquid state by heating them slightly so that after the photolytic deprotection the corresponding gels may be separated very easily from the substrate.

The used gels should preferably have a gel concentration in the range from 20 to 10,000 g/cm$^2$, especially 100 to 1,000 g/cm$^2$. The gel concentration is usually measured by compression tests common to those skilled in the art. In the event that gelatin is used the gel concentration may also be determined by applying the Bloom technique. There, the gel concentration corresponds to the force—in gram—that must be created by a defined cylindrical piston on the surface of a 6.67% gelatin gel (obtained after 17 hours at 10° C.) in order to achieve a depth of depression of 4 mm. The gel concentration so determined then corresponds preferably to a value between 5 and 300 g for gelatin gels in the inventive method.

In the event of application of viscous liquids these liquids should preferably present a dynamic viscosity in the range of 5 to 40,000 mPa·s, particularly 50 to 15,000 mPa·s (measured at 25° C. and for the respective concentration). The type of the polymer compounds is largely uncritical, which means that they are merely expected to result in the desired gels or viscous liquids in the presence of water or the respective solvent. It is hence possible in the inventive method to use a number of synthetic or natural polymers. Among the synthetic polymers polyvinyl alcohol (PVA), polyvinyl acetal, polyacryl amide, polyvinyl pyrrolidone (PVP), polyvinyl acetate, polyethylene imine and Novolake (poly condensation products of phenol and formaldehyde) have been found to be particularly of advantage. According to the invention, gelatins, agarose, agar-agar, pectin, galactomannans, carragheenans, scleroglucans, xanthans and alginates are preferably used among the natural polymers.

In the inventive method, water, a water/$C_1$–$C_4$ alcohol mixture and/or a polar aprotic solvent is used as a solvent for the gel or the viscous liquid. The alcohols, which may be linear or ramified, are used in the mixture with water in a preferred weight ratio of 90/10 to 19/90. The alcohols may contain one or more OH groups and may be selected, in particular, from the group including methanol, ethanol, 1-propanol, 2-propanol, 1-butanol, 2-methyl-1-propanol, 2-butanol, 2-methyl-2-propanol, ethylene glycol, 1,3-propandiol, 1,2-propandiol, glycerin, 1,2-butandiol, 1,3-butandiol, 1,4-butandiol and 2,3-butandiol. The polar aprotic solvents preferably consist of dimethyl sulfoxide (DMSO), dimethyl formamide (DMF), dimethyl acetamide (DMA), aceto nitrile, N-methyl pyrrolidone, diethylene glycol dimethyl ether, tetra ethylene glycol dimethyl ether, sulfolane, 1,3-dimethyl-2-imidazolidinon, 1,3-dimethyl tetra hydro-2 (1H—) pyrimidinon, 2-methoxy-1-methyl ethyl acetate or propylene carbonate.

It is possible within the scope of the present invention to add 0.1 to 10% by weight, more particularly 1 to 5% by weight of additives to the gel or viscous liquid, which enable a rapid photolysis free of secondary reactions as far as possible. Appropriate additives are, for example, accelerators in the form of weak bases such as imidazole, pyrazole, 1-methyl imidazole, 1,8-diazabicyclo [5,4,0]undec-7-ene (DBU), 1,5-diazabicyclo[4,3,0]non-5-ene (DBN), 1,4-diazabicyclo[2,2,2]octane, morpholine, N-methyl morpholine, piperidine, N-methyl piperidine, piperazine, N-methyl piperazine, di-iso propyl ethyl amine, tri-ethyl amine, pyridine, quinoline, collidine, lutidine or picoline. Furthermore, compounds such as urea, thiourea, guanidine hydrochloride, glycine, tris(hydroxy-methyl)-amino methane, tris(hydroxy methyl)amino methane hydrochloride or mannitol, which take a positive influence on the photolysis, have been found to be especially of advantage.

Redox buffers in the form of histidine, polyhistidine, imidazole, thiourea, tris-(hydroxy methyl)nitro methane, sodium azide and/or ascorbic acid are used as further preferred additives for intercepting the free radicals interfering with the photolysis.

Moreover, UV sensitizers, e.g. in the form of benzoic acid or salts of benzoic acid (preferably alkali salts such as sodium or potassium salts) may be added to the gel or viscous liquid in order to accelerate the photolysis. In correspondence with a preferred embodiment additionally consistence-controlling agents are added to the gel or the viscous liquid, respectively, in quantities of 0.001 to 10% by weight, relative to the total weight of the gel or the viscous liquid, on the basis of alkali or alkaline earth salts (such as NaCl, KCl, $CaCl_2$). Within the scope of the present invention it is also possible, however, that the appropriate additives are covalently bound to the polymer compounds and that the latter may be contained in the form of functional groups. Examples of such functionalized polymer compounds are esterified or partly esterified polyvinyl alcohols, for instance.

In order to carry out the inventive method, the nucleoside solution is applied and immobilized on an appropriate substrate. Immobilization may be achieved, for example, by vaporization of the solvent. Additionally, the nucleoside derivatives can be immobilized by covalent bonds on the substrate surface. To this end, a linking agent is covalently applied on the substrate, which presents terminal OH or NH2 functions. These free functional groups are directly operative as in situ starting points for the subsequent photolithographic synthesis of the nucleoside derivatives.

The following nucleoside derivatives or protective groups, respectively, have been found to be particularly of advantage:

5'-O-[2-(4-cyano-2-nitro phenyl) ethoxy carbonyl) thymidine], 5'-O-[2-(2-chloro-6-nitro phenyl)ethoxy carbonyl])thymidine, 5'-O-[2-(2-nitro phenyl)-propoxy carbonyl]thymidine (NPPOC-T), 5'-O-[2-(2-nitro phenyl)propoxy-thiocarbonyl]thymidine, 5'-O-[2-(4-bromo-2-nitro phenyl)propyl sulfonyl]-thymidine, 5'-O-[2-(4-bromo-2-nitro phenyl)propoxy carbonyl] thymidine, 5'-O-[2-(4-iodine-2-nitro phenyl)propoxy carbonyl]thymidine, 5'-O-(α-methyl-2-nitro piperonyl oxy carbonyl)thymidine (MeNPOC-T), 5'-O-[(8-nitro naphth-1-yl)methoxy carbonyl]thymidine, 5'-O-[1-(3-nitro thien-2-yl)]ethoxy carbonyl]thymidine (NTEOC-T), 5'-O-[2-(3-nitro thien-2-yl) propoxy carbonyl] thymidine (NTPOC-T) and 5'-O-[(7-methoxy cumarin-4-yl) methyl oxy carbonyl]thymidine (MCMOC-T).

This substrate surface is subsequently coated with a thin and homogeneous layer of the polymer gel or the viscous liquid, with the coating of the substrate surface being preferably achieved in a spin coating process.

The photolysis of the nucleoside derivatives, which are present in the gel or the viscous liquid in a quasi-dissolved form, can then be carried out, with the exposure commonly taking place from the front side. The photolysis is preferably carried out in a protective gas atmosphere such as nitrogen or argon in order to repress potential secondary reactions as far as possible.

After photolysis, the gel or the viscous liquid is eliminated from the substrate again, which can be achieved in a purely thermal process or else in an appropriate solvent (DMSO, DMF, water) in the case of gels having a comparatively low sol/gel transition temperature.

The advantages of the polymer gels or viscous solutions reside in the fact that they are capable, optionally with suitable additives, to accelerate the photolysis, to intercept secondary products, to orient the (oligo-) nucleotide chains in a suitable manner and to absorb the reaction heat. In this manner, a rapid, defined and complete photo labile deprotection of the nucleoside derivatives is enhanced, which, in turn, leads to the required purity of the synthesized nucleotide or oligo nucleotide sequences.

The invention will now be detailed by means of the following examples.

The application of a viscous solution consisting of polyvinyl alcohol (mean molecular weight 49,000) with a fraction of 4% by weight (balance: water) and 1% by weight of imidazole has been found to be particularly suitable for carrying out the inventive method. This embodiment is described in Example 1, Test No. 18.

EXAMPLES

(1) General

It was possible to establish a model for simulating the photolithographic solid phase synthesis. In this approach, a nucleoside solution is applied on the bottom of a reaction chamber of a micro titration plate. When the solvent is evaporated the nucleoside in photo labile protected form is present on the bottom of the reaction chamber in homogeneous distribution. It can then be irradiated "from the front side" either in "dry" state and/or in a form coated with a gel and/or a viscous liquid of polymer compounds. HPLC is applied for a quantitative analysis of the photolysis. It could be shown by this method that deprotection with dry photolysis is definitely not as good as deprotection with irradiation of a gel or a viscous liquid of polymer compounds.

(2) General Direction for the Exposure with Gels or Viscous Liquids of Polymer Compounds 8 μl of a 0.5 mmole solution (4 μl of a 1 mmole solution) of a photo labile nucleoside in aceto nitrile are applied on the bottom of a micro reaction vessel of a micro titration plate. After a few minutes, the solvent is evaporated. Ideally, 30 μl to not more than 100 μl) of a gel or viscous liquid of polymer compounds are then homogeneously applied (thickness of the layer: 3 to 4 mm). The sample is then irradiated (light source: Hg high-pressure lamp HBO 100 W with interference filter Lambda-max 365 nm, irradiation period: 30 min.). Finally, the irradiated sample is diluted with methanol/water, aceto nitrile/water, aceto nitrile/methanol/water or similar appropriate solvents and injected into the HPLC chromatograph.

Example 1

Irradiation of 5'-O-[2-(2-Nitro Phenyl) Propoxy Carbonyl]thymidine (NPPOC-T)

Irradiation at 365 nm, maximum irradiation period: 30 min

| Test No. | Viscous liquid or gel | yield [%] |
|---|---|---|
| 1 | without viscous liquid or gel | 48 |
| 2 | gelatin med (1% by weight)[4] | 51 |
| 3 | agarose 1[1] (0.5% by weight)[4] (gel) | 66 |
| 4 | PVA[2] (1% by weight)[4] | 98 |
| 5 | PVA[2] (4% by weight)[4] | 99 |
| 6 | PVA[2] (8% by weight)[4] | 77 |
| 7 | PVA[2] (4% by weight)[4] + 1% by weight of glycin | 86 |
| 8 | PVA[2] (4% by weight)[4] + 4% by weight of glycin | 86 |
| 9 | PVA[2] (4% by weight)[4] + 1% by weight of tris | 97 |
| 10 | PVA[2] (4% by weight)[4] + 1% by weight of trisHCl | 74 |
| 11 | PVA[2] (4% by weight)[4] + 1% by weight of tris nitro | 49 |
| 12 | PVA[2] (4% by weight)[4] + 1% by weight of PVP[3] | 56 |
| 13 | PVA[2] (4% by weight)[4] + 1% by weight of Guhy | 93 |
| 14 | PVA[2] (4% by weight)[4] + 1% by weight of urea | 96 |
| 15 | PVA[2] (4% by weight)[4] + 1% by weight of thiourea | 81 |
| 16 | PVA[2] (4% by weight)[4] + 1% by weight of mannitol | 96 |
| 17 | PVA[2] (4% by weight)[4] + 1% by weight of histidine | 99 |
| 18 | PVA[2] (4% by weight)[4] + 1% by weight of imidazole | 100 |

[1] agarose I of the company of Amresco, Solon, Ohio (USA)
[2] mean molecular weight 49,000
[3] polyvinyl pyrrolidone K25 of the company of Fluka, Buchs (Switzerland)
[4] balance: water

Example 2

Irradiation of 5'-O-(α-Methyl-2-Nitro Piperonyl Oxy Carbonyl)thymidine (MeNPOC-T)

Irradiation at 365 nm, maximum irradiation period: 30 min

| Test No. | Viscous liquid | Yield [%] |
|---|---|---|
| 1 | without viscous liquid | 48 |
| 2 | PVA[1] (4% by weight)[3] | 78 |
| 3 | PVA[1] (8% by weight)[3] | 83 |
| 4 | PVA[1] (4% by weight)[3] + 1% by weight of glycine | 79 |
| 5 | PVA[1] (4% by weight)[3] + 4% by weight of glycine | 79 |
| 6 | PVA[1] (4% by weight)[3] + 1% by weight of tris | 78 |
| 7 | PVA[1] (4% by weight)[3] + 1% by weight of tris-HCl | 83 |
| 8 | PVA[1] (4% by weight)[3] + 1% by weight of tris-nitro | 78 |
| 9 | PVA[1] (4% by weight)[3] + 4% by weight of tris-nitro | 79 |
| 10 | PVA[1] (4% by weight)[3] + 1% by weight of PVP[2] | 82 |
| 11 | PVA[1] (4% by weight)[3] + 4% by weight of PVP[2] | 79 |
| 12 | PVA[1] (4% by weight)[3] + 1% by weight of Guhy | 81 |
| 13 | PVA[1] (4% by weight)[3] + 1% by weight of urea | 80 |
| 14 | PVA[1] (4% by weight)[3] + 1% by weight of thiourea | 76 |

[1] mean molecular weight 49,000
[2] polyvinyl pyrrolidone K25 of the company of Fluka, Buchs (Switzerland)
[3] balance: water

Example 3

5'-O-[2-(2-Nitro Phenyl) Propoxy Carbonyl] Thymidine (NPPOC-T)

Irradiation of 365 nm, maximum irradiation period: 30 min

| Test No. | Viscous liquid | Yield [%] |
|---|---|---|
| 1 | without viscous liquid | 48 |
| 2 | PVA[1] (4% by weight), DMSO | 66 |
| 3 | PVA[1] (4% by weight) + 1% by weight of imidazole, DMSO | 73 |

-continued

| Test No. | Viscous liquid | Yield [%] |
|---|---|---|
| 4 | PVA[1] (10% by weight) + 1% by weight of imidazole, DMSO | 98 |
| 5 | PVA[1] (4% by weight) + 1% by weight of 1-methyl imidazole, DMSO | 96 |
| 6 | PVA[1] (8% by weight) + 1% by weight of 1-methyl imidazole, DMSO | 95 |
| 7 | PVA[1] (10% by weight) + 1% by weight of 1-methyl imidazole, DMSO | 88 |
| 8 | PVA[1] (15% by weight) + 1% by weight of 1-methyl imidazole, DMSO | 88 |
| 9 | PVA[1] (4% by weight) + 1% by weight of 1-methyl imidazole, DMA | 97 |
| 10 | PVA[1] (10% by weight) + 1% by weight 1-methyl imidazole, DMA | 75 |
| 11 | PVAcetate[2] (4% by weight), DMSO | 91 |
| 12 | PVAcetate[2] (4% by weight) + 1% by weight of 1-methyl imidazole, DMSO | 81 |

[1] mean molecular weight 49,000
[2] mean molecular weight 170,000

Example 4

Irradiation of 2'-Desoxy-5'-O-[2-(2-Nitro Phenyl) Propoxy Carbonyl]-N$^4$-Phenoxy Acetyl Cytidine (NPPOC-dC$^{PAC}$)

Irradiation at 365 nm, maximum irradiation period: 30 min

| Test No. | Viscous liquid | Yield [%] |
|---|---|---|
| 1 | without viscous liquid | 35 |
| 2 | PVA[1] (4% by weight) + 1% by weight of 1-methyl imidazole, DMSO | 100 |

[1] mean molecular weight 49,000

Example 5

Irradiation of 2'-Desoxy-5'-O-[2-(2-Nitro Phenyl) Carbonyl]-N$^6$-Phenoxy Acetyl Adenosine (NPPOC-da$^{PAC}$)

Irradiation at 365 nm, maximum irradiation period: 30 min

| Test No. | Viscous liquid | Yield [%] |
|---|---|---|
| 1 | without viscous liquid | 44 |
| 2 | PVA[1] (4% by weight) + 1% by weight of 1-methyl imidazole, DMSO | 95 |
| 3 | PVA[1] (10% by weight) + 1% by weight of 1-methyl imidazole, DMSO | 91 |
| 4 | PVAcetate[2] (4% by weight) + 1% by weight of 1-methyl imidazole, DMSO | 90 |

[1] mean molecular weight 49,000
[2] mean molecular weight 170,000

Example 6

Irradiation of 2'-Desoxy-5'-O-[2-(2-Nitro Phenyl) Propoxy Carbonyl]-N$^2$-Phenoxy Acetyl Guanosine (NPPOC-dG$^{PAC}$)

| Test No. | Viscous liquid | Yield [%] |
|---|---|---|
| 1 | without viscous liquid | 36 |
| 2 | PVA[1] (4% by weight) + 1% by weight of 1-methyl imidazole, DMSO | 93 |

[1] mean molecular weight 49,000

Example 7

Irradiation of 5'-O-(α-Methyl-2-Nitro Piperonyl Oxy Carbonyl)Thymidine (MeNPOC-T)

Irradiation at 365 nm, maximum irradiation period: 30 min

| Test No. | Viscous liquid | Yield [%] |
|---|---|---|
| 1 | without viscous liquid | 48 |
| 2 | PVA[1] (4% by weight) + 1% by weight of 1-methyl imidazole, DMSO | 74 |
| 3 | PVA[1] (10% by weight) + 1% by weight of 1-methyl imidazole, DMSO | 72 |

[1] mean molecular weight 49,000

What is claimed is:

1. A method for the specific photolytic splitting off of protective groups from protected nucleoside derivatives immobilized on a substrate, comprising the steps of:

initially applying a layer of a gel or a viscous liquid on the nucleoside derivatives immobilized on said substrate, said gel or said viscous liquid comprising one or more polymer compounds in a concentration of 1 to 20% by weight, relative to the total weight of the gel or viscous liquid, and at least one element selected from the group consisting of water, water/$C_1$–$C_4$ alcohol mixtures and polar aprotic solvents, and photolytically splitting off the protective groups from the protected nucleoside derivatives by exposure to light.

2. The method according to claim 1, wherein the thickness of said viscous liquid is in the range of 0.1 μm to 5 mm.

3. The method according to claim 1, wherein said gel has a sol/gel transition temperature in the range of 15 to 90° C.

4. The method according to claim 3, wherein said gel has a sol/gel transition temperature in the range of 30 to 50° C.

5. The method according to claim 1, wherein said gel has a gel concentration in the range of 20 to 10,000 g/cm$^2$.

6. The method according to claim 5, wherein said gel has a gel concentration in the range of 100 to 1,000 g/cm$^2$.

7. The method according to claim 1, wherein said viscous liquid has a dynamic viscosity in the range of 5 to 40,000 mPa•s at 25° C. and at the respective concentration.

8. The method according to claim 7, wherein said viscous liquid has a dynamic viscosity in the range of 50 to 15,000 mPa•s.

9. The method according to claim 1, wherein said one or more polymer compounds are selected from the group consisting of polyvinyl alcohol, polyvinyl acetal, polyacrylamide, polyvinyl pyrrolidone, polyvinyl acetate, polyethylene imine, novolaks, gelatin, agarose, agar, pectin, galactomannanes, carragheenans, scleroglucanes, xanthans and alginates.

10. The method according to claim 1, wherein said water/$C_1$–$C_4$ alcohol mixture is used in a weight ratio of 90/10 to 10/90.

11. The method according to claim 1, wherein said polar aprotic solvent is selected from the group consisting of dimethyl sulfoxide (DMSO), dimethyl formamide (DMF), dimethyl acetamide (DMA), acetonitrile, N-methyl pyrrolidone, diethylene glycol dimethyl ether, tetraethylene glycol dimethyl ether, sulfolane, 1,3-dimethyl-2-imidazolidinone, 1,3-dimethyl tetrahydro-2(1H) pyrimidinone, 2-methoxy-1-methyl ethyl acetate and propylene carbonate.

12. The method according to claim 1, wherein said gel or said viscous liquid additionally comprises one or more additives in an amount of 0.1 to 10% by weight selected from the group consisting of agents for accelerating photolysis redox buffers and agents for increasing the sensitivity to UV radiation.

13. The method according to claim 12, wherein said one or more additives are present in an amount of 1 to 5% by weight.

14. The method according to claim 12, wherein said agents for accelerating photolysis are selected from the group consisting of imidazole, pyrazole, 1-methyl imidazole, urea, thiourea, guanidine hydrochloride, glycine, tris(hydroxy methyl)amino methane, tris(hydroxy methyl) amino methane hydrochloride and mannitol.

15. The method according to claim 12, wherein said redox buffers are selected from the group consisting of histidine, polyhistidine, imidazole, thiourea, tris(hydroxy methyl)nitro methane, sodium azide and ascorbic acid.

16. The method according to claim 12, wherein said agents for increasing the sensitivity to UV radiation are selected from the group consisting of benzoic acid and salts of benzoic acids.

17. The method according to claim 12, wherein all additives or part thereof are covalently bound to said polymer compounds.

18. The method according to claim 1, wherein said gel or said viscous liquid additionally comprises one or more viscosity modifying agents selected from the group consisting of alkali salts and alkaline earth salts, in an amount of 0.001 to 10% by weight, relative to the total weight of said gel or said viscous liquid.

19. The method according to claim 1, wherein said gel or said viscous liquid is applied on said protected nucleoside derivatives on said substrate by a spin-coating process.

20. The method according to claim 1, wherein the photolytic splitting off is carried out under a protective gas atmosphere.

21. The method according to claim 20, wherein said protective gas atmosphere is nitrogen or argon.

22. The method according to claim 1, wherein the exposure to light is carried out from the side of said substrate with the protected nucleoside derivatives immobilized thereon.

23. The method according to claim 1, wherein after photolytically slitting off the protective groups, said gel is converted into the liquid state by heating and is removed from said substrate.

* * * * *